(12) United States Patent
Vij et al.

(10) Patent No.: US 12,733,992 B2
(45) Date of Patent: Sep. 15, 2026

(54) HARDWARE AND ACCESSORIES SUPPORTING INTRAOPERATIVE CT TRAJECTORY NAVIGATION

(71) Applicant: ClearPoint Neuro, Inc., Solana Beach, CA (US)

(72) Inventors: Kamal Vij, San Marcos, CA (US); Roberto Felipe Rubio, San Marcos, CA (US); Maxwell Jerad Daly, Irvine, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 17 days.

(21) Appl. No.: 18/812,486

(22) Filed: Aug. 22, 2024

(65) Prior Publication Data

US 2025/0064527 A1 Feb. 27, 2025

Related U.S. Application Data

(60) Provisional application No. 63/578,227, filed on Aug. 23, 2023.

(51) Int. Cl.
*A61B 34/20* (2016.01)
*A61B 6/03* (2006.01)
*A61B 6/12* (2006.01)

(52) U.S. Cl.
CPC .............. *A61B 34/20* (2016.02); *A61B 6/032* (2013.01); *A61B 6/12* (2013.01); *A61B 2034/2051* (2016.02)

(58) Field of Classification Search
CPC ............ A61B 6/03; A61B 6/032; A61B 34/20
See application file for complete search history.

(56) References Cited

U.S. PATENT DOCUMENTS 6,267,769 B1 * 7/2001 Truwit .................. A61B 90/11 606/1
10,376,333 B2 8/2019 Piferi et al.
11,253,333 B2 2/2022 Piferi et al.
2008/0200798 A1 * 8/2008 Eklund ................. A61B 90/11 600/414
2015/0202008 A1 * 7/2015 Grant .................... A61B 34/71 606/34
2021/0282866 A1 9/2021 Vij et al.
2023/0414862 A1 12/2023 Stigall et al.
(Continued)

FOREIGN PATENT DOCUMENTS

WO WO-2023/168327 A2 9/2023
WO WO-2023/205156 A1 10/2023

*Primary Examiner* — Chao Sheng
(74) *Attorney, Agent, or Firm* — Mintz Levin Cohn Ferris Glovsky and Popeo PC

(57) ABSTRACT

Systems and methods are configured to adjust a surgical trajectory pursuant to a surgical intervention. The systems and methods are configured to grossly align an aiming device to the target surgical trajectory wherein the aiming device is coupled to a patient. An intraoperative computerized tomography (iCT) scan is used to obtain an image of a surgical field. An actual trajectory of a CT-visible element is obtained and extended forward down to a surgical plan's target depth for comparison to the target surgical trajectory. The actual trajectory is adjusted to obtain an adjusted trajectory prior to insertion of a device via the aiming device into the patient.

25 Claims, 6 Drawing Sheets

(56) References Cited

U.S. PATENT DOCUMENTS

| | | | |
|---|---|---|---|
| 2024/0042625 | A1 | 2/2024 | Williams |
| 2024/0261537 | A1 | 8/2024 | Williams et al. |
| 2024/0374317 | A1 | 11/2024 | Williams et al. |

* cited by examiner

HARDWARE AND ACCESSORIES SUPPORTING INTRAOPERATIVE CT TRAJECTORY NAVIGATION

CROSS REFERENCE TO RELATED APPLICATION

The present application claims priority to U.S. Provisional Application No. 63/578,227, filed on Aug. 23, 2023, and entitled "HARDWARE AND ACCESSORIES SUPPORTING INTRAOPERATIVE-CT TRAJECTORY NAVIGATION," the entirety of which is incorporated by reference herein.

BACKGROUND

There is a need for more accurate implementations of a surgical trajectory pursuant to a surgical intervention such as in a brain of a patient.

SUMMARY

Disclosed are devices, systems and methods that enable accurate forward projection of a surgical trajectory to improve final placement accuracy in a standard operating room by leveraging intraoperative computerized tomography (iCT) scan. In a non-limiting example, surgery is performed on a brain wherein a surgical trajectory is through the brain. Pursuant to the disclosed method, a user adjusts the surgical trajectory prior to inserting an interventional device (such as a stylet, catheter, drug delivery device, cannula, needle, therapeutic device, etc.) into the brain to minimize or reduce deviation from an original surgical plan. The disclosed method reduces the overall number of brain penetrations per procedure on average and reduces total procedure time.

The details of one or more variations of the subject matter described herein are set forth in the accompanying drawings and the description below. Other features and advantages of the subject matter described herein will be apparent from the description and drawings, and from the claims.

DETAILED DESCRIPTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

Figure 1:
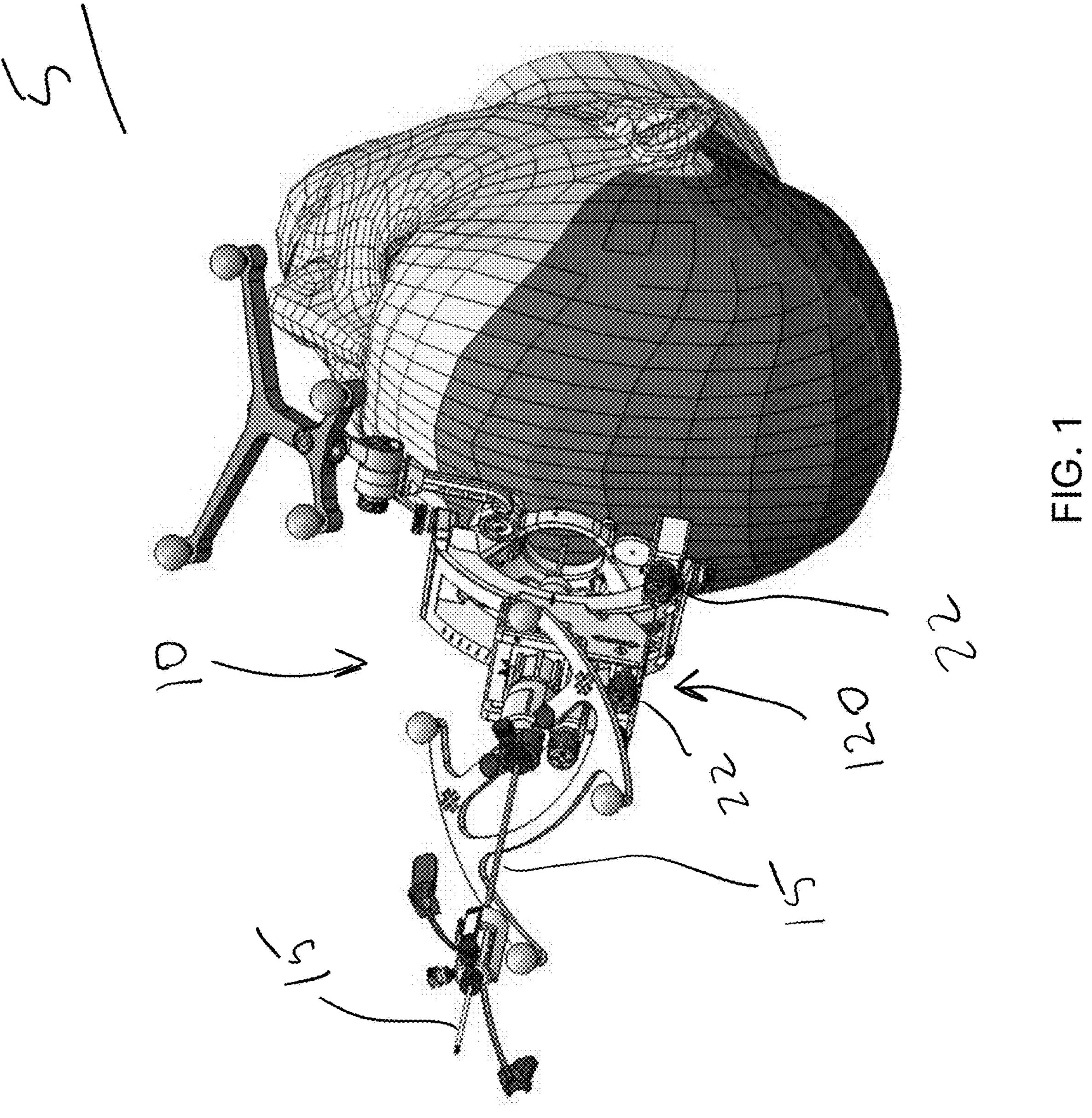
FIG. 1 shows a schematic representation of a system of device that can be used pursuant to the method described herein.

FIG. 1 shows a precision trajectory aiming system 5 that includes a frameless-stereotaxic precision trajectory aiming device 10 (such as SmartFrame by ClearPoint Neuro, Inc.) and a CT-visible device (such as a ceramic stylet 15) positioned in line with a predefined, initial surgical trajectory prior to any insertion of the stylet 15 into anatomy. The CT-visible device can vary and can be, for example, a cannula, a needle, a drug delivery device, a therapeutic device, a catheter, and/or a component of the trajectory aiming system such as the device guide 102 of the aiming device 10 or a portion thereof. The stylet 15 is an elongated body that extends along a long axis. The system 5 further includes an XY stage 20 attached to the frameless-stereotaxic precision trajectory aiming device 10. The XY stage 20 has one or more continuous adjustment actuators or dials 22 that can be actuated (such as via rotation of the dials) to adjust an XY-axis trajectory of the system into a brain of a patient, as described further below. The XY stage provides adjustments in at least the roll, pitch, X, and Y directions by turning the appropriate dials 22 as described further below. The dials 22 can be turned manually by a user or in conjunction with a motor directly or indirectly to the dials 22.

The system 5 is mounted on the patient's head such as by positioning the frameless-stereotaxic precision trajectory aiming device 10 on the patient's head. The system 5 is oriented such that the stylet 15 extends along an initial trajectory grossly aligned to a target or target trajectory of a predetermined surgical plan. The aiming device 10 positioned such that the axis of the stylet 15 is grossly aligned to the surgical plan's proposed, initial trajectory wherein the initial trajectory grossly points to a target using optical navigation or other means prior to insertion of the stylet into the brain. In a non-limiting example, the surgical plan is obtained prior to attaching the system 5 to the patient's skull. For example, a magnetic resonance imaging (MRI) process can be obtained to plan the procedure in combination with a computed tomography (CT) for registration of a trajectory of the plan. The resultant MRI and CT images are fused together. The scan encompasses the relevant regions of the trajectory such as for example the entire head region where the plan includes the skull. The resultant surgical plan includes a target location(s) as well as entry location(s) into the anatomy.

Figure 2:
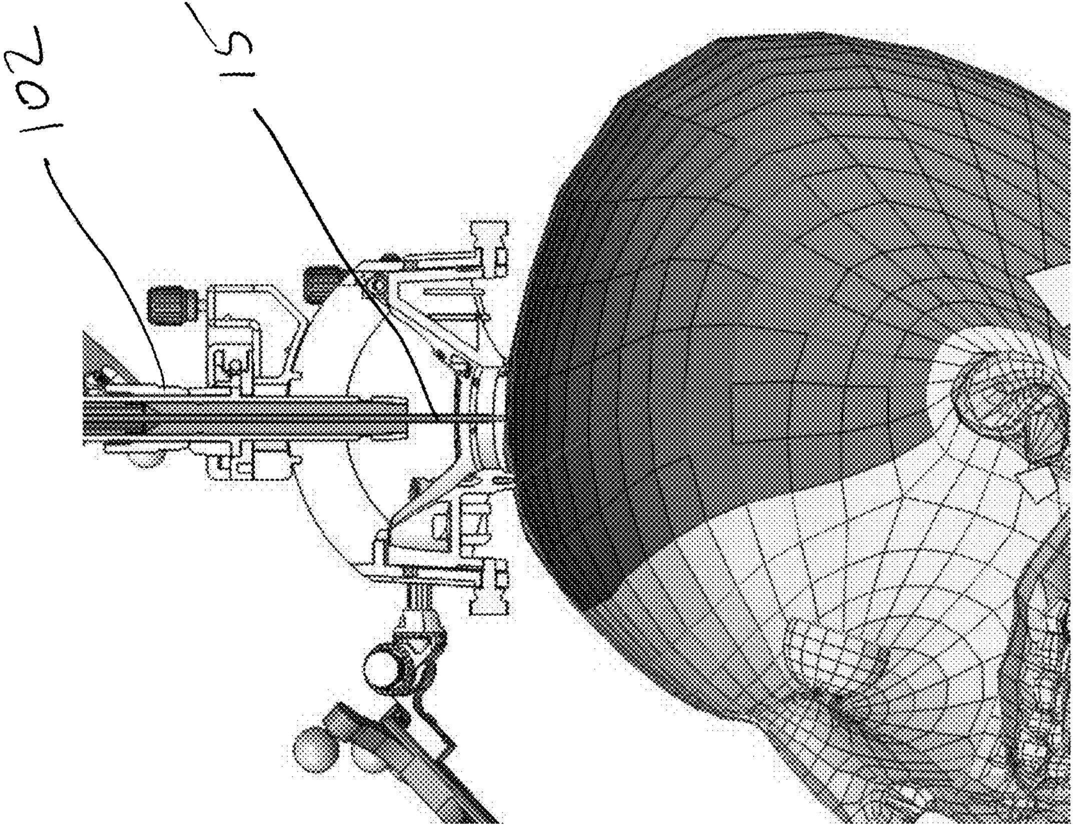
FIG. 2 shows a stylet of the system positioned for insertion in a brain.
Figure 3:
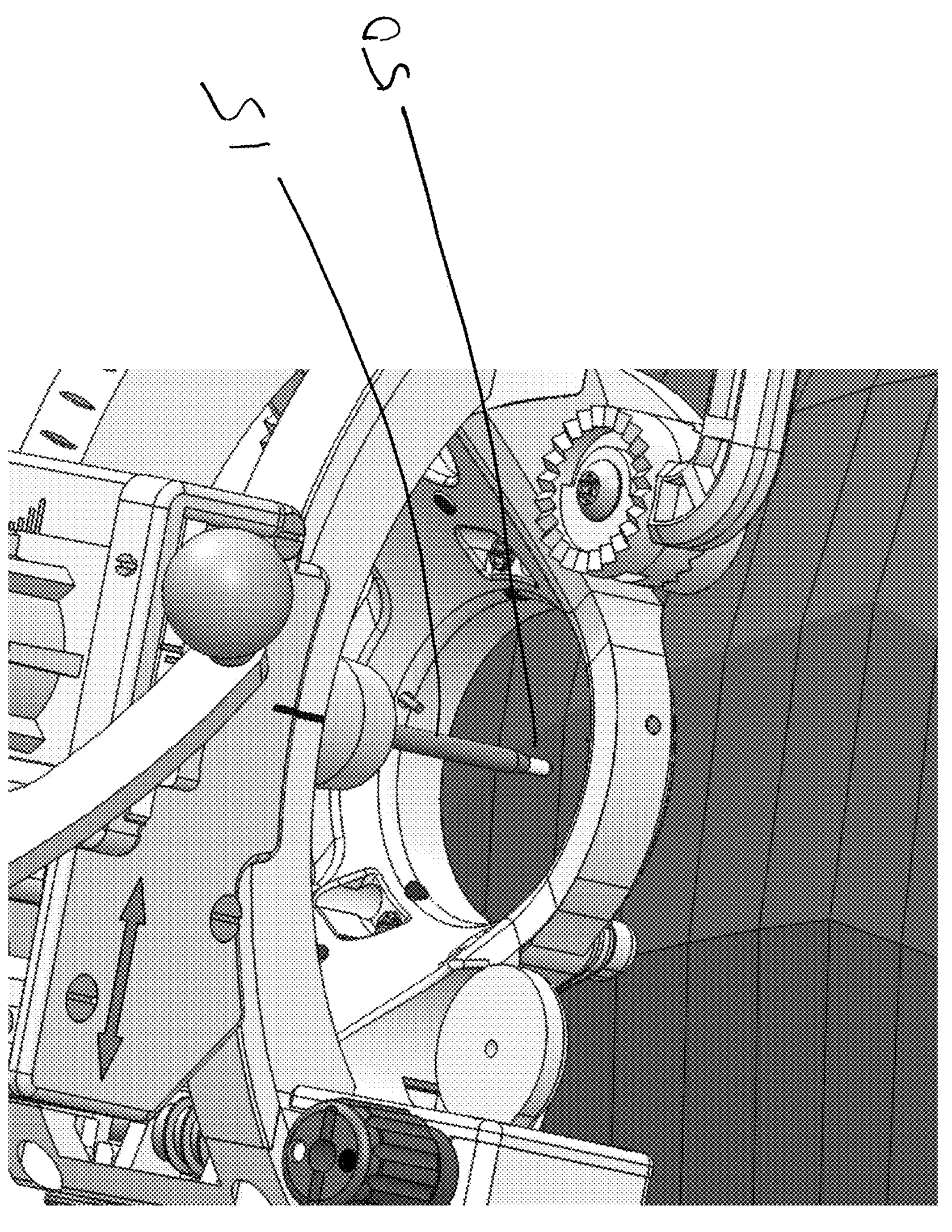
FIG. 3 shows another view of the stylet.

FIG. 2 shows the stylet 15 mounted in the aiming device and positioned for insertion into a brain of the patient. The stylet 15 has a distal tip 50 (which can be sharpened) (FIG. 3) that is positioned just adjacent a surface of the brain's dura matter. The aiming device 10 is initially in a position such that the stylet 15 can be grossly aligned with the predetermined, initial surgical trajectory. After such gross alignment, a user places the ceramic stylet 15 into a support column or device guide 102 of the aiming device 10. The guide 102 has a central lumen through which a sheath (such as a peel away sheath) and ceramic stylet or other suitable devices can be placed and oriented relative to the trajectory. In an embodiment, the guide 102 or a portion thereof is CT visible. As shown in FIG. 3, the ceramic stylet 15 is not yet inserted into the brain pursuant to one or more initial steps. Rather, the distal tip 50 of the ceramic stylet 15 can be positioned just adjacent a surface of the brain's dura matter. Once the stylet 15 is positioned as such, a user then runs a scan of the patient, such as an iCT scan, to obtain an image with a portion of the uninserted stylet 15 and the full desired trajectory in an image showing a field of view. A virtual extension of the stylet's actual trajectory down to target depth is created (such as by drawing the virtual extension on an image) to provide an indication of the trajectory of the stylet. The virtual extension can correspond to, be defined by, or aligned with a long axis of the stylet.

The user can cause a stylet trajectory (such as in the form of a visible stylet trajectory line on an image) to be drawn from the proximally visible tip of the ceramic stylet 15 down through a distal end of the ceramic stylet. (Or the trajectory can be drawn relative to the guide 102 or other device coupled to the aiming device.) On the image, the stylet trajectory line is extended distally down to the predetermined surgical plan's target at depth for comparison. The user can cause the image to be rotated to match the XY orientation of how the aiming device was mounted on the patient's head. Next, the user actuates the XY stage 20 to refine or adjust the stylet trajectory closer to the originally planned surgical target trajectory. For example, the user can adjust the continuous adjustment dials 22 (FIG. 1) on the XY stage to refine or adjust the trajectory closer to the originally planned surgical target trajectory. After such adjustment, the stylet trajectory can then be compared to the predetermined surgical trajectory and a projected error between the stylet trajectory and the predetermined surgical trajectory can be calculated. One or more scans (such as CT scans) can then be iteratively obtained and additional adjustments to the XY stage can be performed until the error between the stylet trajectory and predetermined surgical trajectory is within a desired range based on comparison between the two.

After finalizing the stylet trajectory, the ceramic stylet 15 is inserted into the brain with accuracy that exceeds methods using only optical navigation or other traditional methods alone.

The device used for virtually extending the trajectory down to a predetermined target depth is CT-visible and maintains a consistent center of axis suitable for a highly accurate forward projection prior to insertion. As mentioned, the CT visible device can be the stylet or a portion of the aiming device as well as other devices such as a cannula, a needle, a drug delivery device, a therapeutic device, or a catheter.

The precision trajectory aiming system 5 is configured such as in an optimized manner to function with optical navigation systems that may include workflows for performing deep brain stimulation (DBS) electrode lead placement procedures. The optical navigation system can include a position tracking camera and software that are programmed to recognize navigation wand(s) with spherical geometries that interface with the trajectory aiming system.

The disclosed system and method can sometimes be referred to as a PIVOT (Pre-Insertion Verification of Trajectory) system or method. The disclosed systems and methods utilize the previously obtained iCT image to calculate a trajectory projection prior to device insertion and may prescribe additional X-Y frame adjustments to improve placement accuracy. The benefit of forward projection trajectory assessment pursuant to the disclosed system and method can be comparable to MRI-guidance with the using a navigation system by ClearPoint Neuro, Inc. although there are some differences. Pursuant to MRI-guidance, three imaging fiducials are embedded in a frameless stereotaxy mount along with a fluid-filled targeting cannula, which are then imaged and used for a software to segment and perform geometric calculations. The MRI-guidance software automatically calculates deviation from surgical plan and then provides the surgeon with directional dial-turn instructions to bring the forward projection closer to the original surgical plan.

In contrast, the disclosed system and method uses a CT-visible device (such as the stylet 15) that is visible within the actual pre-insertion image itself to establish at least two points along it that represent the trajectory to target if an insertion were to occur without any adjustments. A virtual extension line is then drawn down to the predetermined target depth based on the presurgical plan. A probe's eye view or perspective in navigation software is then rotated (such as via user interaction) to match the mounted frame's XY orientation in how it was affixed to the patient skull. After the user draws measuring lines to quantify the forward projection's deviation from the original surgical plan, those measures can be translated into appropriate dial turns based on predetermined specifications. In a non-limiting example, one rotation of either an X dial 22 and/or Y dial 22 converts to exactly 1 mm change at target wherein fractions of such a change at target require a corresponding fraction of a dial turn. This can result in adjustments to actual trajectory in a sub millimeter range by making appropriate rotation(s) to the X dial 22 or the Y dial 22.

The following United States patent documents describe related systems and methods and are incorporated herein by reference in their entirety: (1) U.S. Pat. No. 10,376,333 "Devices For Surgical Navigation Systems"; (2) U.S. Pat. No. 11,253,333 "Devices For Surgical Navigation Systems"; (3) US Patent Publication No. 2021/0282866 "Image-Guided Surgical Systems With Automated Trajectory Guide Systems And Related Devices And Methods"; (4) Provisional Patent Application No. 63/483,368, "Trajectory Tracking Probe For Surgical Optical Navigation Systems."

Figure 4:
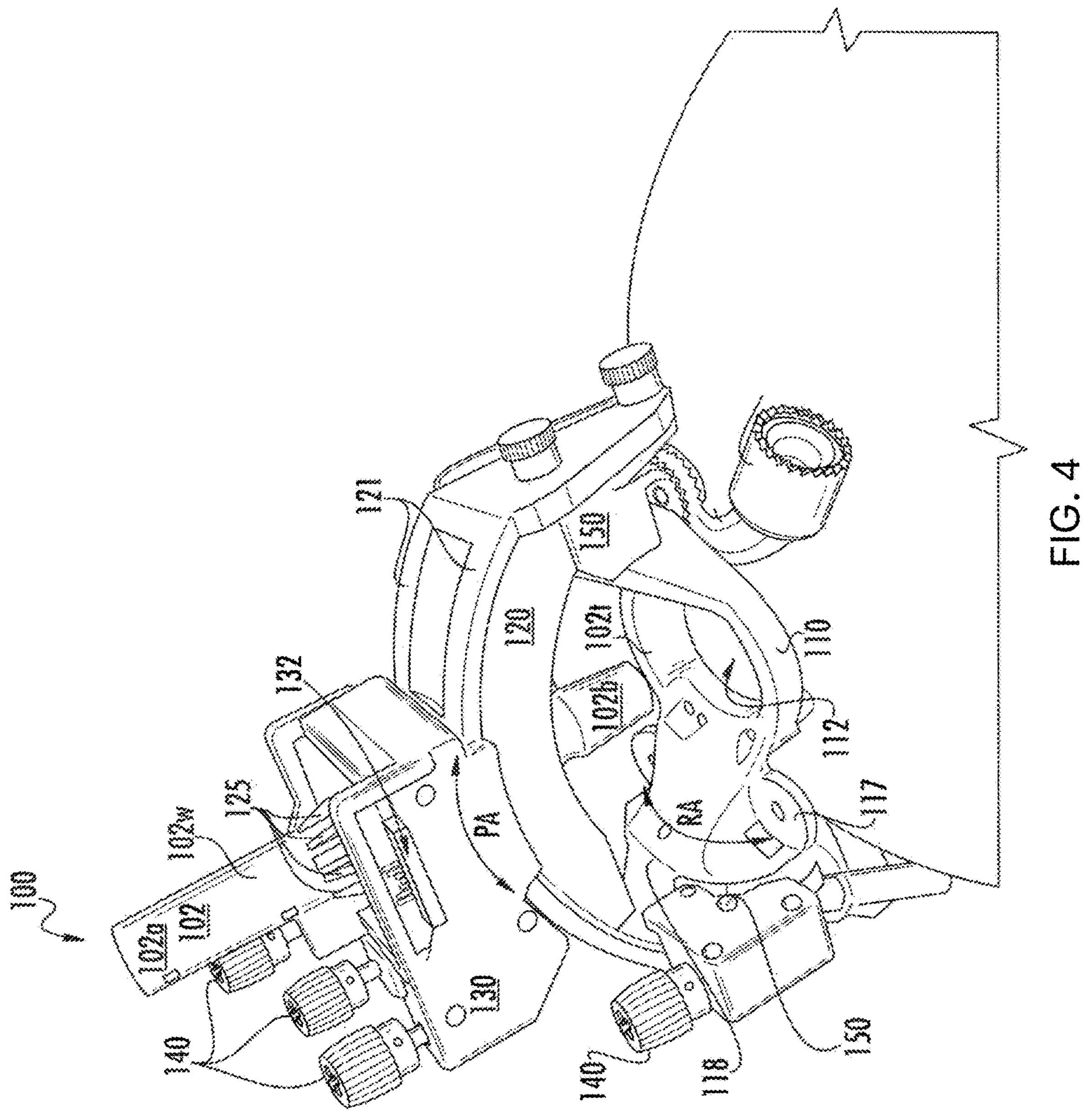
FIGS. 4 and 5 shows a non-limiting example of the frameless-stereotaxic precision trajectory aiming system.
Figure 5:
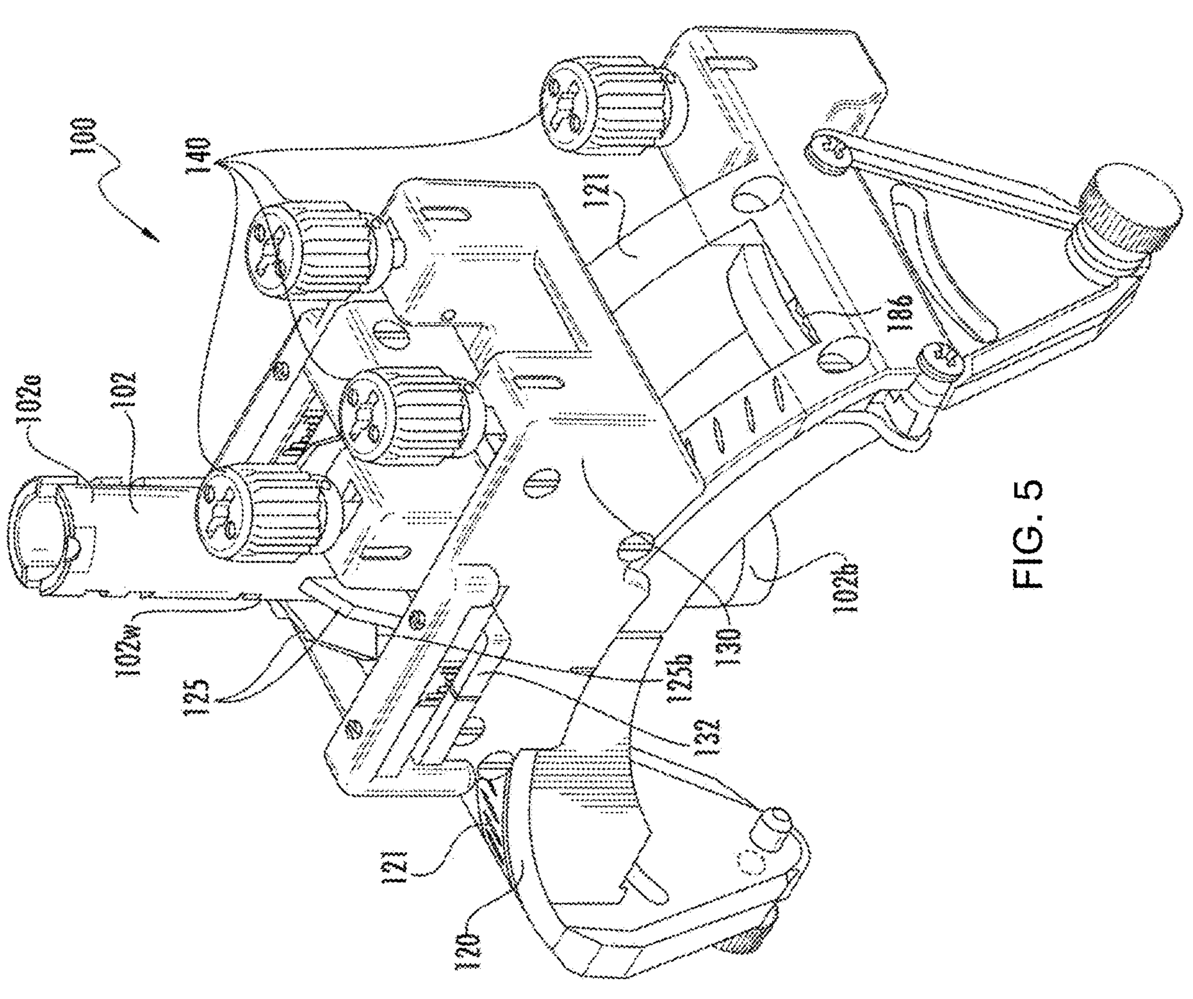

FIGS. 4 and 5 shows a non-limiting example of the frameless-stereotaxic precision trajectory aiming device 10. It should be appreciated that FIGS. 4 and 5 show an example and that the features disclosed herein are not limited to use with the device shown in FIGS. 4 and 5. The trajectory frame aiming device 10 includes a support column 102, a platform 130 and typically an X-Y table 132 held by the platform 130. The support column 102 can be held by the platform 130 so that a proximal end 102*a* resides above the platform and a distal end 102*b* resides below the platform 130 and above a patient access aperture 112 formed by a base 110 attached to the platform 130. The base 110 can attach to the skull of a patient or other target objects or positions. The platform 130 can be attached to a yoke 120. The yoke 120 can be attached to arcuate arms 150 that extend up from the lower end of the base 110. At least one of the arcuate arms 150 can have an upper surface with a thread pattern 118 that can cooperate with a worm gear 186 in the yoke 120. Actuators 140 (which correspond to the dials 22) can be used to rotate the yoke 120 relative to the arm(s) 150, rotate the platform 130 relative to the yoke 120, and move the X-Y table 132 in X and Y directions. This results in a corresponding rotation or movement of the trajectory of a stylet coupled to the device.

The yoke 120 can have a pair of control arcs 121 that cooperate with the platform 130 to provide pitch and roll adjustments. The X-Y table 132 can allow for X-Y adjustments of the trajectory. The yoke 120 is rotatable about a roll axis RA (FIG. 4). The platform 130 is movably mounted to the yoke 120 and is rotatable about a pitch axis PA (FIG. 4.) The X-Y support table 132 can be configured to move in an X-direction (side to side) and Y-direction (front to back) relative to the platform 130 by actuation of the actuators 140. The assembly 100 can include circumferentially spaced apart fins 125 attached to an outer wall 102*w* of the support column 102. The fins 125 can extend radially outward from the wall 102*w* of the support column 102, typically so that a bottom surface 125*b* resides against an upper surface of the X-Y table 132.

The system can be modified to enhance usability in a variety of manners. For example, the trajectory aiming system's guide channel 102 can include material that forms a CT-visible layer suitable for forward projection techniques. Such an embodiment removes the need to prepare a separate device (e.g. ceramic stylet) and insert it for an iCT scan resting on the dura of the patient. Furthermore, the stylet 15 that is prepared for forward-projection scan can include a hollow lumen chamber having a uniform or consistent inner diameter. Such a consistent diameter can provide improved contrast points for the user or software to automatically detect the device's center of axis across its length.

In another embodiment, the height of the system is shortened so it barely extends beyond a height of the tower or outside of the iCT field of view (FOV). A safety-device can be permanently affixed to the proximal tip of the device as a measure to prevent unintended insertion of the tip into cortex of the patient. A side-loading, secondary depth stop can also be included for individually adjusting a length for the distal end to rest on unviolated dura.

In another embodiment, the frameless-stereotaxy trajectory aiming device includes a modified mount with CT-visible orientation indicators. This can make it easier for the user or software to detect the frame's orientation mounted on the patient's head. This information can be used to more intuitively rotate the probe's eye view image to match the orientation of the mounted frame. After the CT scan is acquired pursuant to the method, it can be easier to translate any measured deviations from the surgical plan's target into directly actionable turns with the XY stage dials.

In another embodiment, the system includes a software module configured to instruct or assist a user on making the appropriate adjustments to the knobs 22 for the XY frame. In addition, Digital Imaging and Communications in Medicine (DICOM) coordinates for the PIVOT trajectory's projected tip at the target plane, and the DICOM coordinates of the target point, can be exported to the software module. The software module calculates a distance (such as in both X and Y directions or to make gross adjustments to pitch and roll knobs of the frame) to translate the trajectory's projected tip at the target plane to the intended target point. The software module then provides information to a user regarding the number of turns (or partial turns) for the Pitch, the Roll, the X and/or the Y adjustment knobs 22, and the direction of rotation (such as in clockwise or counterclockwise directions) to accomplish the recommended PIVOT adjustment of the stereotactic trajectory. Such information can be presented to a user on a display of a computer device including a mobile device.

In addition, the system can include a motor module attached directly to the adjustment knobs 22 on the stereotactic frame to automatically provide precise adjustment of the X-Y stage and/or pitch and/or roll knobs. In conjunction with the software module described above, the motor modules can automatically make the exact adjustments needed to perform the recommended adjustments pursuant to the method.

In another embodiment, the software module is electronically connected to a CT scanner such that CT images can be electronically transferred to a workstation running the software module. After the frame is mounted to the patient, a quick low dose CT scan is acquired. As the frame and base are visible in CT images they can be automatically detected, and their location can be determined. The low dose CT scan can be registered to pre-op hi resolution CT and MRI scans. The software module calculates adjustment of all four knobs for aligning the frame to desired trajectory. The software module then automatically makes the knob adjustments using the motor module. One more low dose CT scan is then required to verify the frame position pursuant to the method.

Pursuant to a method, an MRI image and a CT image are obtained of the surgical field. The two images are fused together. The aiming device 10 is mounted to the patient such as to the skull of the patient. In a specific and non-limiting embodiment of the method, at least some of the following steps are performed:

1) Align the aiming device frame's trajectory using the pitch and roll knobs as informed by the optical navigation's onscreen feedback.
2) Tighten both roll lock screws to strengthen the frame's ability to maintain the aligned trajectory.
3) Obtain the insertion depth from an appropriate software or device navigation technique.
4) Measure the ceramic stylet and prepare a peel-away sheath assembly.
5) Add a secondary depth stop to the ceramic stylet such as approximately 145 mm from the distal tip of the stylet (such as to prevent any possibility of accidental slippage that may impact the dura).
6) Insert the ceramic stylet into the frame to the level of dura without disturbing the dura.
7) Obtain a new iCT scan. In an example case of the skull, the field of view is sufficiently positioned to capture superior elements above the skull including the frame and as much of the stylet as possible.
8) Import the new scan and merge the scan to create an adjusted new trajectory in the navigation software. The creation of the new trajectory may be done without modifying any elements of the previously existing trajectory plan. The new surgical plan is used to assess and compare the existing trajectory alignment to a desired surgical plan.
9) Set the entry point of the new plan at on a center axis of the most proximal point of the ceramic stylet as seen in the resulting image.
10) Set the target of the new plan at the most distal end of the ceramic stylet where the tip rests on the dura.
11) Extend a resulting line down to the actual surgical target's depth.
12) Rotate the probe's eye view in the navigation to match the orientation of how the mount/frame is affixed to the patient's skull (thus making any changes made to the XY align with XY directional axis).
13) Scroll forward to target depth and measure the difference between the forward projection trajectory and the actual surgical target in terms of an X-axis change and separately a Y-axis change.
14) Convert the measured differences into X and Y dial changes (corresponding to the dials 22). In a non-limiting example, 1 mm=1 full rotation of a knob in the corresponding direction and fractional millimetric measures equated to fractional rotations.
15) Run an optional iCT scan to rerun the protocol and making corresponding adjustments as necessary.
16) Pierce the dura using a lancet.
17) Insert the ceramic stylet and the sheath to the target.
18) Measure the desired depth on a deep brain simulation (DBS) lead.
19) Swap the ceramic stylet for the DBS lead and run an optional iCT to confirm placement of the lead itself.

20) Peel the remainder of the peel-away-sheath.
21) Secure the anchoring device onto the DBS lead.
22) Mark the lead, remove the DBS stiffening stylet, and pull the lead down through the SF OR tower.
23) Remove the SF OR tower, secure the 'monocle' cover, and properly close the incision.

It should be appreciated that the aforementioned steps are an example and that deviations from these steps are within the scope of this disclosure.

Example Computing System

Figure 6:
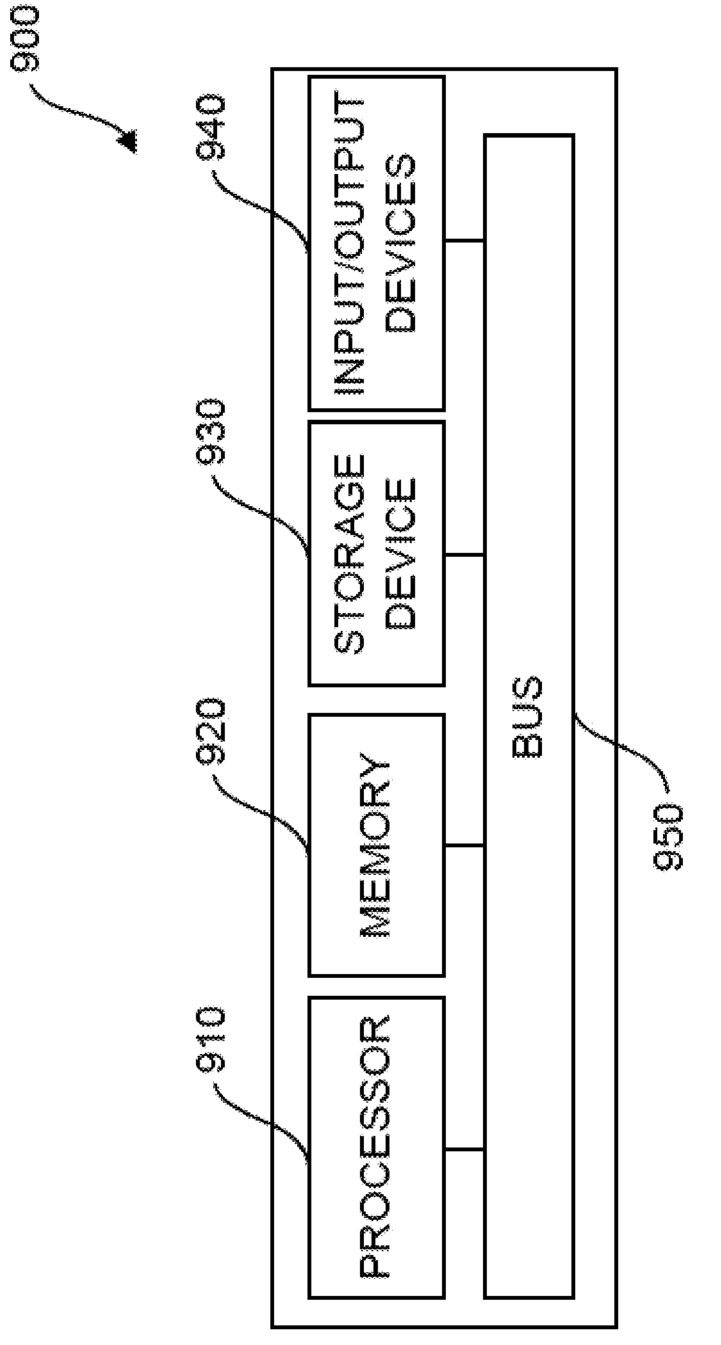
FIG. 6 depicts a block diagram illustrating an example of a computing system consistent with implementations of the current subject matter.

FIG. 6 depicts a block diagram illustrating an example of a computing system 900 consistent with implementations of the current subject matter. The computing system 900 may implement processes and methods described herein. The system can include or be coupled to an imaging system, an interactive user interface, and/or an inputs program to receive and manipulate physical, biometric, biomechanical, material and mechanical information and data. The system 900 can be communicatively coupled to or include an imaging device such as a CT or MR device.

As shown in FIG. 6, the computing system 900 can include a processor 910, a memory 920, a storage device 930, and input/output device 940. The processor 910, the memory 920, the storage device 930, and the input/output device 940 can be interconnected via a system bus 950. The processor 910 is capable of processing instructions for execution within the computing system 900. Such executed instructions can implement one or more components of, for example, VESA, 3D-ID AI, and/or MP Tool. In some implementations of the current subject matter, the processor 910 can be a single-threaded processor. Alternately, the processor 910 can be a multi-threaded processor. The processor 910 is capable of processing instructions stored in the memory 920 and/or on the storage device 930 to display graphical information for a user interface provided via the input/output device 940.

The memory 920 is a computer readable medium such as volatile or non-volatile that stores information within the computing system 900. The memory 920 can store data structures representing configuration object databases, for example. The storage device 930 is capable of providing persistent storage for the computing system 900. The storage device 930 can be a floppy disk device, a digital cloud, a hard disk device, an optical disk device, or a tape device, or other suitable persistent storage means. The input/output device 940 provides input/output operations for the computing system 900. In some implementations of the current subject matter, the input/output device 940 includes a keyboard and/or pointing device. In various implementations, the input/output device 940 includes a display unit for displaying graphical user interfaces.

According to some implementations of the current subject matter, the input/output device 940 can provide input/output operations for a network device. For example, the input/output device 940 can include Ethernet ports or other networking ports to communicate with one or more wired and/or wireless networks, Bluetooth or digital cloud system (e.g., a local area network (LAN), a wide area network (WAN), the Internet).

In some implementations of the current subject matter, the computing system 900 can be used to execute various interactive computer software applications that can be used for organization, analysis and/or storage of data in various (e.g., tabular) format (e.g., Microsoft Excel®, and/or any other type of software). Alternatively, the computing system 900 can be used to execute any type of software application. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities, plug ins, or can be standalone computing products and/or functionalities. Upon activation within the applications, the functionalities can be used to generate the user interface provided via the input/output device 940. The user interface can be generated and presented to a user by the computing system 900 (e.g., on a computer screen monitor, etc.). The user interface can be integrated with other devices or virtual ecosystems.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random-access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input or output devices include touch screens or other touch-sensitive devices such as single or multi-point resistive or capacitive track pads, joy sticks, voice recognition hardware and software, optical scanners, optical pointers, digital image capture devices and associated interpretation software, image scanners including computer topography and magnetic resonance (MR) imaging systems and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A method of adjusting a surgical trajectory pursuant to a surgical intervention, comprising:

obtaining a target surgical trajectory into a patient;

grossly aligning an aiming device to the target surgical trajectory wherein the aiming device is coupled to the patient;

coupling a CT-visible element to the aiming device;

using intraoperative computerized tomography (iCT) scan to obtain an image of a surgical field;

obtaining an actual trajectory of the CT-visible element and extending forward the actual trajectory down to a surgical plan's target depth for comparison to the target surgical trajectory;

causing a line representative of the actual trajectory to be shown on the image wherein the line corresponds to a long axis of the CT-visible element;

adjusting the actual trajectory to obtain an adjusted trajectory prior to insertion of a device via the aiming device into the patient.

2. The method of claim 1, wherein the CT-visible element comprises a cannula, a needle, a drug delivery device, a therapeutic device, or a catheter.

3. The method of claim 1, wherein the actual trajectory is defined by a forward extension of a long axis of a stylet inserted into the aiming device.

4. The method of claim 1, wherein the surgical trajectory includes a brain of the patient as a surgical target.

5. The method of claim 1, further comprising inserting a stylet into the brain along the adjusted trajectory.

6. The method of claim 1, wherein the adjusted trajectory reduces or eliminates a deviation in trajectory relative to an original surgical plan.

7. The method of claim 1, wherein the surgical intervention relates to a deep brain stimulation electrode lead placement procedure.

8. The method of claim 1, wherein the line is straight.

9. The method of claim 1, wherein coupling the CT-visible element to the aiming device comprises positioning a CT-visible stylet into the aiming device.

10. The method of claim 9, wherein the CT-visible stylet is inserted into the aiming device without inserting the stylet into the patient.

11. The method of claim 9, wherein the stylet is initially positioned with a distal tip of the stylet adjacent dura matter of a brain.

12. The method of claim 9, wherein the stylet is a ceramic stylet.

13. The method of claim 12, wherein the ceramic stylet has a hollow lumen.

14. The method of claim 1, wherein adjusting the actual trajectory comprises:

rotating the image to match an XY orientation of how the aiming device was mounted on the patient's head; and using adjustment dials on an XY stage to refine the actual trajectory closer to target surgical trajectory.

15. The method of claim 14, wherein the adjustment dials include an X adjustment dial and a Y adjustment dial.

16. The method of claim 14, wherein the adjustment dials are manually rotated by a user to obtain an X adjustment and a Y adjustment.

17. The method of claim 14, wherein the adjustment dials are coupled to a motor.

18. The method of claim 17, wherein the motor automatically rotates the adjustment dials.

19. The method of claim 1, further comprising automatically calculating a deviation between the target surgical trajectory and the actual trajectory.

20. The method of claim 19, further providing directional dial-turn instructions for an XY stage.

21. The method of claim 1, further comprising:

obtaining the surgical trajectory;

after obtaining the surgical trajectory, attaching the aiming device to the patient's skull.

22. The method of claim 21, further comprising:

placing a stylet into the aiming device after attaching the aiming device to the patient's skull.

23. The method of claim 22, extending the line distally down on the image to a target depth of the surgical plan for comparison.

24. The method of claim 23, further comprising adjusting the aiming device so an error between the line representative of the actual trajectory and the target surgical trajectory is within a desired range on an image.

25. The method of claim 24, wherein the stylet is coupled to a peel-away sheath, and further comprising peeling the peel-away sheath from the stylet.

* * * * *